(12) United States Patent
Een et al.

(10) Patent No.: US 6,170,636 B1
(45) Date of Patent: Jan. 9, 2001

(54) APPLICATION DRUM FOR USE IN THE PRODUCTION OF ABSORBENT ARTICLES

(75) Inventors: Hans Een, Mölnlycke; Lennart Nilsson, Skärhamn; Jan-Erik Hallin, Kallered; Kent Edgren, Mölnlycke, all of (SE)

(73) Assignee: SCA Hygiene Products AB, Gothenburg (SE)

( * ) Notice: Under 35 U.S.C. 154(b), the term of this patent shall be extended for 0 days.

(21) Appl. No.: 09/194,970
(22) PCT Filed: Jun. 2, 1997
(86) PCT No.: PCT/SE97/00951
  § 371 Date: May 13, 1999
  § 102(e) Date: May 13, 1999
(87) PCT Pub. No.: WO98/00356
  PCT Pub. Date: Jan. 8, 1998

(30) Foreign Application Priority Data

Jun. 28, 1996 (SE) .................................. 9602565

(51) Int. Cl.[7] .................................................. B65G 47/84
(52) U.S. Cl. .......................................... 198/441; 198/471.1
(58) Field of Search .................................. 198/438, 441, 198/471.1; 156/567, 568

(56) References Cited

U.S. PATENT DOCUMENTS

| | | |
|---|---|---|
| 2,980,231 * | 4/1961 | Mahaffy et al. ................ 198/441 |
| 3,823,809 | 7/1974 | Henry et al. . |
| 4,523,671 * | 6/1985 | Campbell ........................ 198/441 |
| 4,789,419 | 12/1988 | Hermann . |
| 5,070,994 * | 12/1991 | Focke .............................. 198/441 |

FOREIGN PATENT DOCUMENTS

| | | |
|---|---|---|
| 2165495 | 7/1992 | (DE) . |
| 2074127A | of 1881 | (GB) . |
| 768724 | 10/1980 | (RU) . |
| WO87/00403 | 1/1987 | (WO) . |
| WO95/19752 | 7/1995 | (WO) . |
| WO96/23470 | 8/1996 | (WO) . |

\* cited by examiner

*Primary Examiner*—Christopher P. Ellis
*Assistant Examiner*—Mark A. Deuble
(74) *Attorney, Agent, or Firm*—Burns, Doane, Swecker & Mathis, L.L.P.

(57) ABSTRACT

The invention relates to an application drum for use in the production of absorbent articles. The application drum has a longitudinal axis of rotation and comprises material engagement means on the outside thereof for both collecting and delivering a material component. In order to be able to use only a single drum and still be able to place material components more to one or the, other side of the center-line of a conveyor belt, the material engagement means is arranged for reciprocal movement with respect to the drum in a direction parallel to the axis of rotation of the drum.

10 Claims, 2 Drawing Sheets

APPLICATION DRUM FOR USE IN THE PRODUCTION OF ABSORBENT ARTICLES

FIELD OF THE INVENTION

The invention relates to a device as defined in the first part of claim 1.

BACKGROUND TO THE INVENTION

Application drums, or lay-down drums as they are often called, are known in the prior art. The drums are used in production of absorbent products such as nappies, incontinence articles and the like. The drums are provided with material engagement means which receive a piece of material from a supply means and then apply it to an underlying sheet of an absorbent product positioned on a moving conveyor belt. The receiving location and the delivery location are typically 180° opposed and the drum rotates continuously so as to pass through the receiving location and then the delivery location.

The piece of material may be of any type, but is typically a pre-formed piece, such as an absorbent core or other absorbent layer. The engagement means is generally arranged so that an under-pressure (e.g. a vacuum)is applied to the material engagement means on the drum when the article is in the collecting position. The under-pressure is applied through perforations in the engagement means.

The under-pressure is maintained on the material engagement means as the drum rotates, until the drum has rotated so that the material piece attached thereto is in contact with the conveyor belt, or the part-formed absorbent article thereon. An over-pressure is then applied to the engagement means so as to secure release of the material piece from the application drum.

In lateral production techniques, the absorbent articles being formed are typically placed head-to-toe across the conveyor belt (i.e. one article is rotated 180° with respect to the next). If, as is normal, a material piece must be laid onto the part-formed articles at a location which is not in line with, or to one side of, the centreline of the drum, then two laterally-spaced application drums (or a similar arrangement) are often used. In such a case, each of the drums delivers a material piece to alternate ones of the part-formed products.

The use of two independent drums is of course more expensive, may require complicated synchronisation between the drums and the material supply equipment and normally involves more auxiliary equipment (such as pumps and pressure lines for example). A great deal of space may also be required, especially where the drums must be longitudinally offset with respect to each other as well as being transversely offset. Further disadvantages will be apparent to the man skilled in the art. To summarise, the use of two application drums is thus clearly undesirable.

SUMMARY OF THE PRESENT INVENTION

The present invention has the object of overcoming the aforementioned problems by providing an improved application drum. The essential features of the drum are defined in claim 1, whilst preferred features of the drum are defined in the dependent claims.

Due to the reciprocal movement of the engagement means as defined in claim 1, a single drum is provided which can be used for applying material pieces at varying transverse locations on a longitudinally-travelling conveyor belt.

The preferred features of the invention defined in the dependent claims allow a simple and reliable construction to be obtained.

BRIEF DESCRIPTION OF THE DRAWINGS

The invention will now be described in more detail with reference to a preferred embodiment thereof as depicted in the drawings, in which.

DETAILED DESCRIPTION OF A PREFERRED EMBODIMENT OF THE INVENTION

Figure 1:
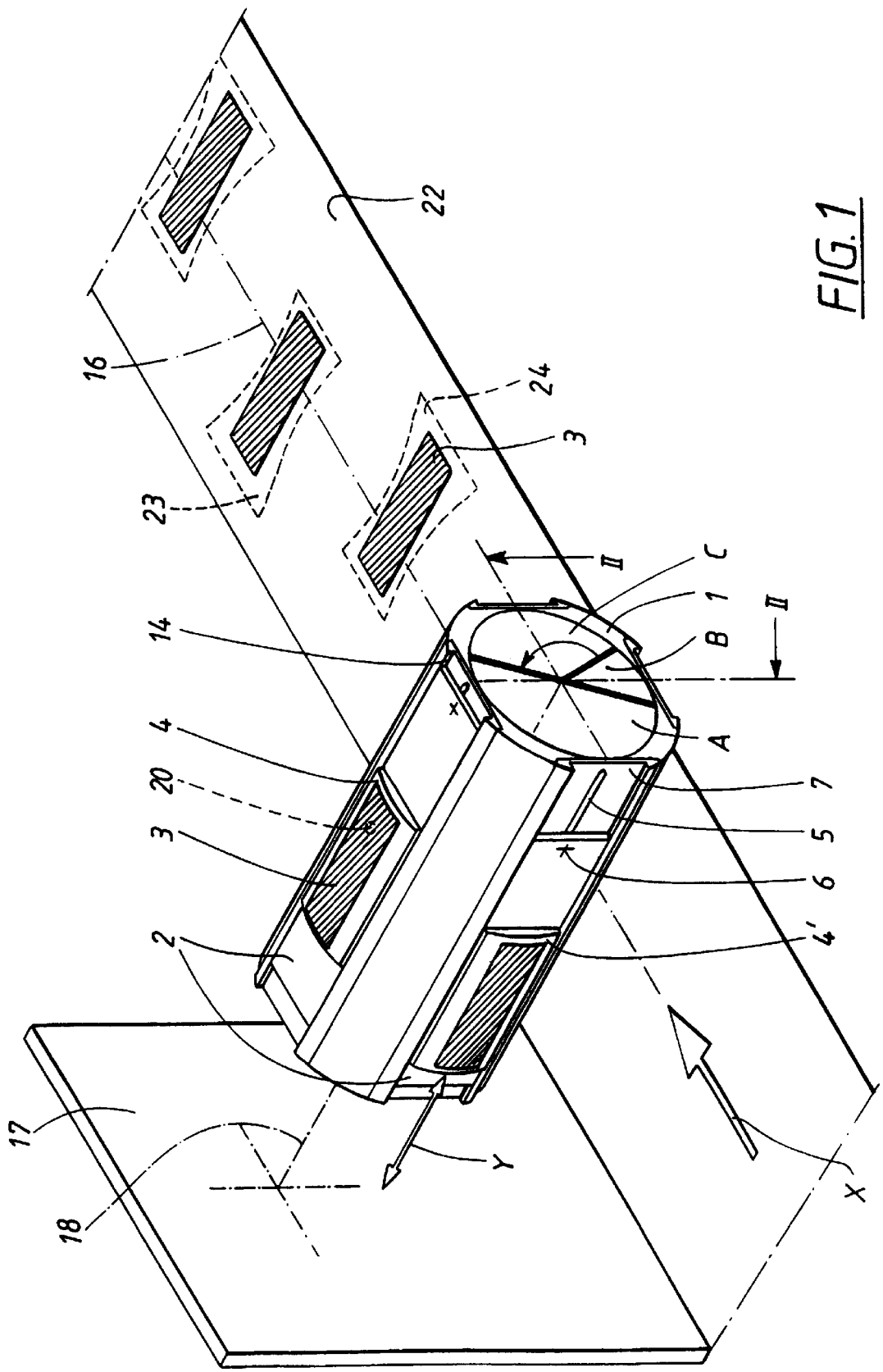
FIG. 1 is a perspective view of a drum in accordance with the invention, depicting the main features visible from the outside of the drum.

FIG. 1 shows an application drum, generally denoted as 1, positioned above a conveyor belt 22 having a centre-line 16. The conveyor belt is driven in a direction "X" shown by the arrow upstream of the drum. The application drum 1 rotates about its longitudinal axis of rotation 18 shown in chain-dotted lines. The axis 18 will most commonly be a shaft, supported for rotation on a support 17.

On the conveyor belt 22, a plurality of absorbent articles 23, 24 being formed are indicated in phantom lines. The absorbent articles are normally asymmetric and are placed in a head-to-toe relationship as shown. Although not depicted as such, the absorbent articles 23, 24 may be connected to one another to form a connected web of absorbent articles which are later separated.

The drum has four material engagement means 4, 4' thereon, only two of which are visible in FIG. 1. Said engagement means are positioned at 90° intervals around the surface. It is possible however to use only one material engagement means if desired, although the manufacturing operation will be slower. In the embodiment shown however, the material engagement means 4, 4' are arranged as two opposed pairs, each of said engagement means in one pair being offset by 180° with respect to the other.

It is also possible to use two or more material engagement means instead of four as indicated above.

Each engagement means is arranged for reciprocal movement in a direction Y with respect to the drum 1. In the example shown, material engagement means 4 at the uppermost position on the drum 1 is in a collection position. In said collection position a material piece 3 is supplied thereto from a supply device (not shown) such as a conveyor belt or a supply wheel. In an advantageous embodiment of the invention, the centre of the collection position is substantially in line with the axis 16 of the conveyor belt. Similarly the central axis 21 (see FIG. 2) of the drum is preferably in line with axis 16 of the conveyor belt.

As the drum rotates in an anti-clockwise direction as shown, the material engagement means 4 rotates therewith. During rotation, the material engagement means 4 is displaced to the right (looking from the view point in FIG. 1) by an arrangement which will be described below. When it reaches its lowermost position (i.e. 180° displaced to its shown position), the material piece 3 will have moved far enough to the right so that it will be in a correct position to be applied on the article 24, at a location which is more to one side of the axis 16 of the conveyor belt. The material piece 3 is then removed from the means 4 and applied to the article 24.

During continued rotation of the drum 1, the material engagement means 4 will be reciprocated back to its substantially central location on the drum 1, for picking up a subsequent material piece.

The material engagement means 4' undergoes similar movements as the drum rotates. However, instead of being moved to the right of the axis 16 (or centre-line 21) as engagement means 4, it is moved in the opposite direction, allowing it to be placed in the correct location on the articles 23 which are displaced towards the left side of the conveyor belt 22.

As will be clear to the reader, the articles 23, 24, may be centrally located with reference to the axis 16, but the material pieces 3 are often required to be placed in a non-symmetric position on said articles.

In order that the material pieces 3 can be temporarily attached to the engagement means 4, 4' and then released therefrom, the engagement means are formed with perforations 20, through which air over-pressures or air under-pressures may be applied to the surface of means 4. Thus, in the embodiment shown, an under-pressure is applied in the collection position (i.e. the uppermost position) and is maintained in a material holding zone until the delivery or deposition zone (lower position) is reached. These zones are indicated by zones "A" and "B" respectively in FIG. 1.

In zone "C", where no material piece 3 is attached to the engagement means, a gradually increasing under-pressure may be applied or no pressure at all. However, an over-pressure may be applied to allow any small remaining fragments of the material piece 3 to be expelled before a new material piece 3 is received. If expulsion is used, e.g. by means of an over-pressure, a suitable collection device (not shown) for collecting the remaining small fragments should preferably be arranged.

Each of the material engagement means 4, 4' is positioned on a separate respective carriage member 2 in the form of a plate. In turn, the carriage member is guided for reciprocal movement with respect to the drum by means of guide sections inserted onto the drum as modular units. Each guide section has a flat support surface 7 and shallow guiding walls 14 which slidingly engage with the outer walls of the plate. In this way a reciprocal movement, strictly parallel to the drum axis 18 can be ensured. Exact parallel movement is not however an absolute pre-requisite since small variations will not substantially effect the performance of the final absorbent product.

In order to control the reciprocal movement of the carriage members 2, a guide element 6 in the form of a connection means is provided between the carriage members 2 (the plates) and a control means, in the form of a cam, placed inside the drum 1. The guide element 6 is in the form of a pin which is attached (e.g. by having a threaded end thereon for a lock nut) at its outer end to the carriage member 2. At its inner end, the pin is provided with a member having a cam engagement surface. The pin passes through a slot 5 provided in the support surface 7.

Figure 2:
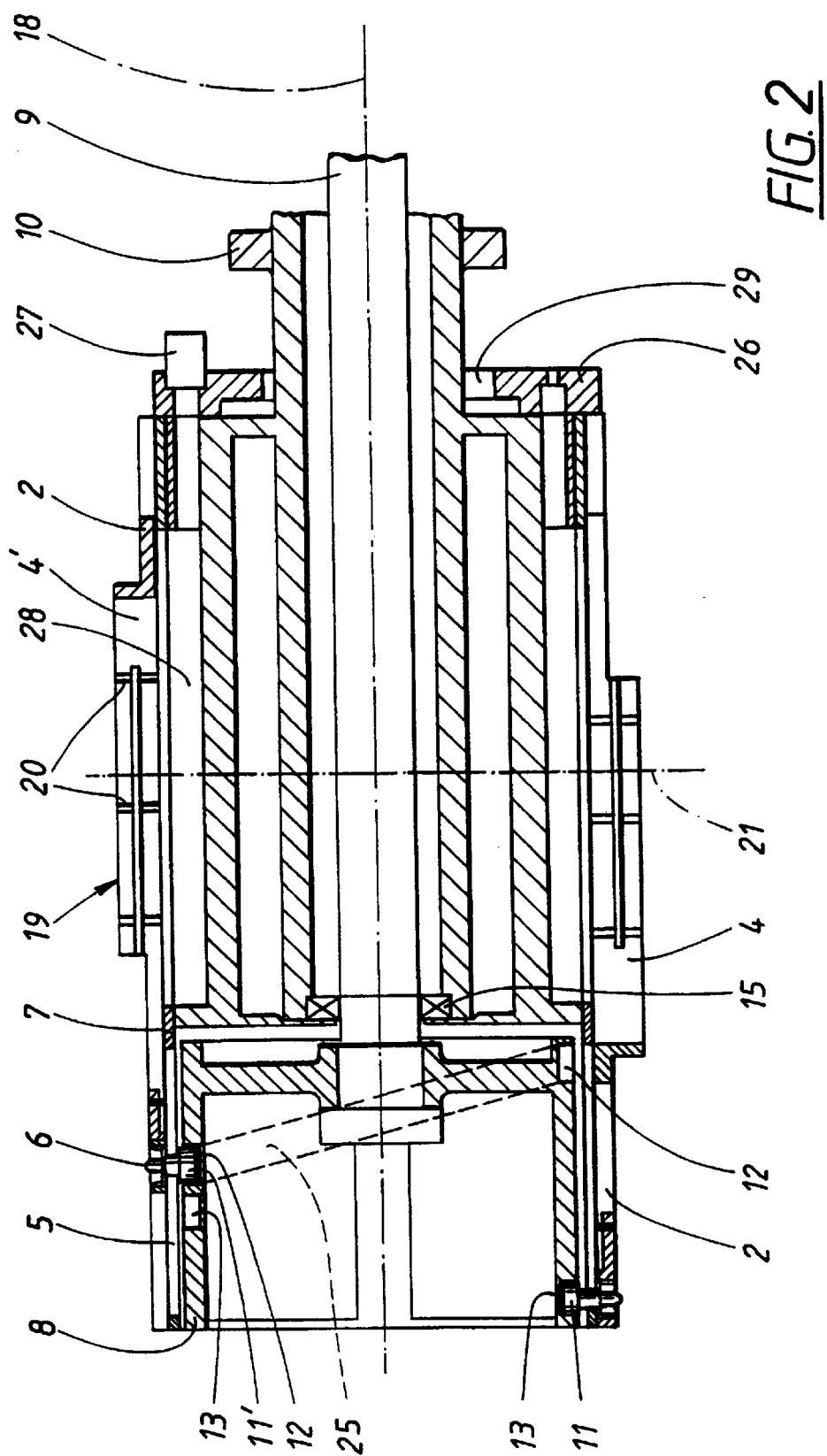
FIG. 2 is a cross-sectional view, viewed in a direction along the rotational axis of a simple application drum as seen through line II—II.

In the embodiment shown in FIG. 2, the inner end is provided with a cam engagement surface in the form of a cam follower 11' such as a cam roller which is adapted to fit into a continuous cam curve 12 provided on a fixed cylindrical drum 8 (see FIG. 2).

As will be clear from FIG. 2, which is a view through line II—II in FIG. 1, and not merely a simple vertical section through drum 8, the cam curve 12 as depicted at its uppermost point in FIG. 2 corresponds to a position of about 90° before the top position shown in FIG. 1. At the top position shown in FIG. 1 however, the cam curve starts at a location which is close to the middle of the drum 8 surface. The cam curve is arranged such that the cam follower 11' will then be displaced to the right, or to the left, from this generally central location, depending on which engagement means, 4 or 4', is concerned. An example of part of a cam curve is shown as 25 in dotted lines.

As can be seen in FIG. 2, two cam curves 12, 13 are provided, one for each of the pairs of carriage members (plates) 2 and respective means 4', 4 and rollers 11', 11.

Thus, the two different cam curves 12, 13 allow the plates to move in different directions (to the left or to the right in a direction Y) from the material piece collection position which is uppermost in FIG. 1.

A drive device (not shown) is connected to a drive element 10, such as a gear wheel, in order to rotate the application drum 1 and the carriage members 2 connected thereto. The cam drum 8 is however maintained in a fixed position and one end of the drum 1 is supported on a bearing 15, for example, for rotation with respect to the fixed drum shaft 9 running therethrough. However, for adjustment, the cam drum may be releasably lockable to allow it to be rotated and then relocked before operation commences.

In order to provide the zones A, B and C with the correct over-pressure or under-pressure, a pressure supply device 27 and a pressure control plate 26 (which is fixed in space) are provided. The pressure control plate 26 has a hole 29 therein for passage of the drum 1 drive shaft. The pressure control plate 26 is slidingly engaged against the rear end (the right-hand end in FIG. 2) of the drum 1.

Air pressure (under-pressure or over-pressure) is supplied to the perforations 20, which are preferably present substantially all the way along zone 19, by means of airways 28 between the plates 2 and the drum 1. The particular configuration of the control plate 26 allows air pressure to be correctly applied at the desired locations during rotation of the drum 1. Further details of the pressure plate are not indicated here as this is not part of the present invention and not required for understanding the principles of the present invention.

Cam curves 12, 13 on a cam drum have been shown in FIG. 2 as examples of cam control members. Such an arrangement has the particular advantage of being simple and reliable, with a minimum of moving elements. However, more complicated systems could be used such as those comprising hydraulically or pneumatically actuated members used to displace the guide elements 6, or even the carriage members 2 directly.

It is to be understood that the invention described hereinabove is not limited to the preferred embodiment shown in FIGS. 1 and 2, but can be varied widely within the scope of the appended claims.

What is claimed is:

1. An application drum for use in the production of absorbent articles and for applying a material component onto the absorbent articles, whereby said application drum has a longitudinal axis of rotation, and wherein said application drum comprises material engagement means on the outside thereof which both collects the material component and applies the material component onto the absorbent articles, wherein said material engagement means is arranged for reciprocal movement with respect to said application drum, said movement being in a direction which is substantially parallel to the axis of rotation of said application drum.

2. An application drum according to claim 1, wherein said material engagement means is attached to a carriage member, and in that said drum is provided with guiding members for guiding said carriage member.

3. An application drum according to claim 2, wherein said carriage member is a platelike member.

4. An application drum according to claim 1, wherein said material engagement means has a guide element attached thereto, said guide element passing through a slot in said application drum.

5. An application drum according to claim 4, wherein said guide element comprises a cam-follower, said cam follower being guided in a continuous cam curve positioned inside said application drum.

6. An application drum according to claim 5, wherein said cam curve is provided in the surface of a substantially fixed cylindrical drum element.

7. An application drum according to claim 5, wherein there are a plurality of material engagement means, each connected with a respective cam follower, and in that there are two separate cam curves, within a respective one of which curves said respective cam follower is engaged.

8. An application drum according to claim 1, wherein said material engagement means reciprocates between a receiving position located proximate to the centre-line of said application drum and a delivery position located away from the centre-line of said application drum.

9. An application drum according to claim 8, wherein a plurality of engagement means is provided around the perimeter of said application drum, sequential ones of said engagement means being arranged to be displaced in opposite directions with respect to their receiving position on said drum.

10. An application drum according to claim 1, wherein the receiving and delivery of said material component occurs by using means supplying an under-pressure and an over-pressure respectively, said pressures being applied through a surface of said material engagement means which is provided with perforations.

* * * * *